United States Patent [19]

Burk

[11] Patent Number: 4,504,982
[45] Date of Patent: Mar. 19, 1985

[54] ASPHERIC INTRAOCULAR LENS

[75] Inventor: Paul O. Burk, Glendora, Calif.

[73] Assignee: Optical Radiation Corporation, Azusa, Calif.

[21] Appl. No.: 405,326

[22] Filed: Aug. 5, 1982

[51] Int. Cl.³ .......................... A61F 1/16; A61F 1/24
[52] U.S. Cl. .......................................................... 3/13
[58] Field of Search .................. 3/13, 1; 351/160, 161

[56] References Cited

U.S. PATENT DOCUMENTS 4,010,496  3/1977  Neefe ........................................ 3/13

FOREIGN PATENT DOCUMENTS 1103399  5/1955  France ..................................... 3/13
 939016 10/1963  United Kingdom .................... 3/13

OTHER PUBLICATIONS

American Journal of Optometry and Archives of American Academy of Optometry, vol. 36, Jun. 1959, No. 6, "Problems and Compromises in the Design of Aspheric Cataract Lenses", John K. Davis, Southbridge, MA, pp. 279-288.
"The Design of Intra-Ocular Lenses", M. Jalie, Dept. of Applied Optics, City and East London College, Final Version Received May 1978, pp. 1-21.
"Designing a New Intra-Ocular Lens", M. Jalie, Prin. Lecturer, Dept. of Applied Optics, City and East London College, 4/28/1979, *The Ophthalmic Optician*, pp. 300, 302, 304, 305 & 306.

*Primary Examiner*—Ronald L. Frinks
*Attorney, Agent, or Firm*—Christie, Parker & Hale

[57] ABSTRACT

An intraocular lens for permanent implantation into a human eye is provided. The lens has at least one aspheric surface.

6 Claims, 6 Drawing Figures

U.S. Patent  Mar. 19, 1985  4,504,982
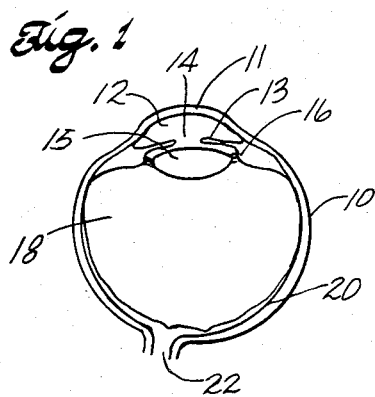
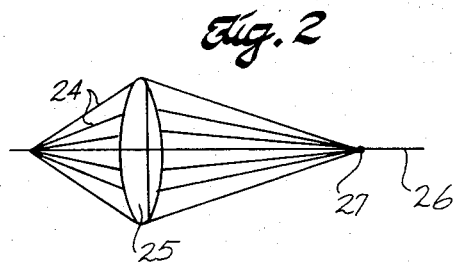
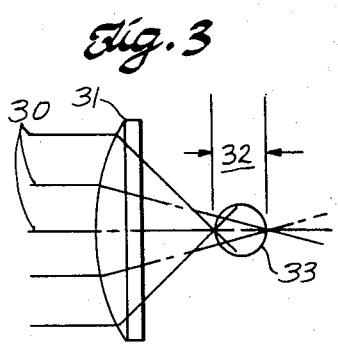
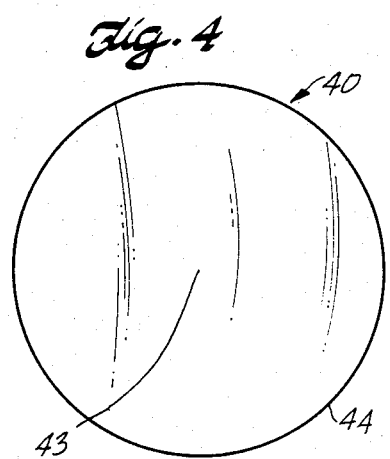
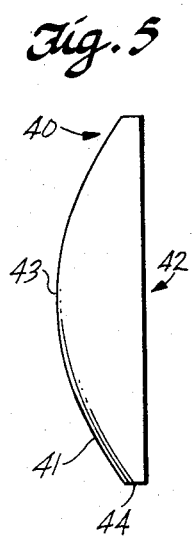
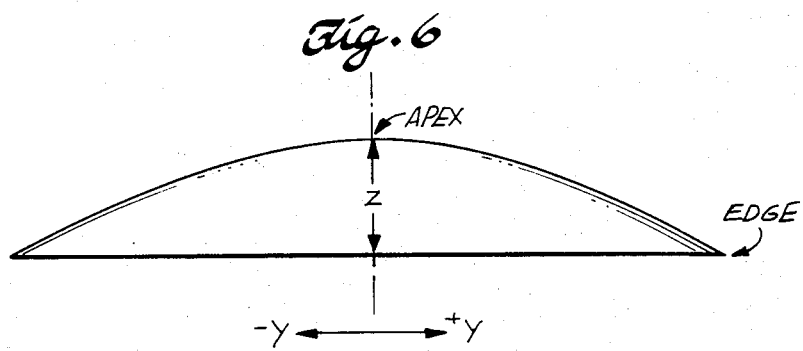

ASPHERIC INTRAOCULAR LENS

FIELD OF THE INVENTION

This invention relates to intraocular lenses and more particularly to an improved intraocular lens.

BACKGROUND OF THE INVENTION

The problem of restoring useful vision to a human eye after its cataractous natural lens has been removed has been with us since the introduction of cataract surgery. The solution to this problem has included the use of spectacle lenses, contact lenses, and permanent implantation into the eye of a man-made lens, i.e., an intraocular lens.

Since 1949, when the first implant of an intraocular lens was made, hundreds of thousands of persons have had such implants. Recent advances in cataract surgery have now made the intraocular lens implant procedure a safer and more popular alternative. For example, it is estimated that nearly 40% of the people now undergoing cataract surgery select a lens implant, i.e., an intraocular lens, instead of wearing contact lenses or thick cataract-type spectacles.

In addition to advances in surgery which enhance the desirability of intraocular lens implants, there have also been advances in the design of such lenses. Two significant advances in intraocular lens design have been the use of ultrasound eye measurements to determine lens prescriptions and the use of surgical keratometers to reduce visual aberrations (astigmatism) produced by the incision on the cornea. In light of these advances, it is estimated that between about 72 and 82% of intraocular lens implant patients achieve 20/40 vision or better.

A lens implant differs from contact lenses and cataract spectacles in that it is permanently implanted within the eye. This 24-hour vision correction has been considered an advantage by proponents of lens implants. The intraocular lens must sufficiently meet the visual requirements of the patient without a natural lens. The lens implant has proven in many cases to restore a normal level of activity to the aged cataract patient. Ideally, the lens implant should provide the same or better visual acuity and comfort as that of healthy crystalline lenses before removal.

Most senior citizens express a need to avoid dependence upon relatives and friends and to avoid institutionalization in a nursing home. One of the key factors in maintaining an independent life style for senior adults in the ability to maintain a driver's license. Vision of 20/40 is obtained by a majority of lens implant patients which meets the driver's license requirements in most states.

While the vision of the post-operative cataract patient tested in the eye doctor's office is often adequate to qualify for a driver's license, serious visual deficits are reported in night vision among some patients including double images, halos around light, glare, and ghost images.

Light rays of different wavelengths within the visible color spectrum are all refracted at different angles, and thus do not converge on a unique focal point. This is known as chromatic aberration. Of greater consequence is spherical aberration. This is the inherent aberration of spheric lenses caused by the fact that the lens has a longer focal length for rays near the center than for rays passing through the outer zone. Spherical aberration is commonly attributed by surgeons as the cause of patient complaints of visual flare, glare, halo or "dazzle" and "glitter".

These aberrations are not generally present where the natural crystalline lens is healthy and performing its function. Principally the aberrations are avoided in that the lens is aspherically shaped and causes a variation in refractive index at different distances from the edge wherein the index is higher in the center and relatively lower at the edges.

Attempts have been made to correct for these aberrations in spectacles and contact lenses where the natural lens has been removed. See, for example, *Problems and Compromises In The Design of Aspheric Cataract Lenses*, American Journal of Optometry, Vol. 36, No. 6, June 1959. Further, the possibility of an aspheric intraocular lens is mentioned by M. Jalie in an article entitled *The Design of Intra-Ocular Lenses*, British Journal of Physiological Optics, Vol. 32, Pages 1–22, 1978 and in an article entitled *Designing A New Intra-Ocular Lens*, The Ophthalmic Optician, Apr. 28, 1979 but it is suggested that the uncertainty inherent in any attempt to duplicate the performance of the human eye at wide pupil diameters may obviate any advantage that an aspheric surface provides.

SUMMARY OF THE INVENTION

This invention relates to an intraocular lens for implantation into a human eye. The lens is aspheric in that it has a plurality a radii of curvature from the apex to the edge with the radii generally increasing away from the apex. This aspheric lens eliminates most of the spherical aberrations by the use of the progressively longer radii towards the outer zone of the lens.

DRAWINGS

These and other features, aspects, and advantages of the present invention will be more fully understood when considered with respect to the following detailed description, appended claims, and accompanying drawing, wherein:

FIG. 1 is a schematic horizontal section of an eyeball;

FIG. 2 is a diagram of a theoretical spheric lens producing a single focal point from a point source.

FIG. 3 is a diagram of the focusing of collimated rays by an actual spheric lens and the resultant spherical aberration.

FIG. 4 is a plan view of an exemplary embodiment of an intraocular lens provided in accordance with the practice of principles of this invention.

FIG. 5 is a side view of the intraocular lens of FIG. 4.

FIG. 6 is a schematic of a lens showing the convention for the coordinates Z and Y.

DETAILED DESCRIPTION OF THE DRAWINGS

In FIG. 1, there is shown a schematic of an eyeball about the horizontal middle section. The eyeball is formed by an outer shell 10 that is filled principally with a jelly-like substance (vitreous humor) which maintains the shape. The front portion of the eyeball is the cornea 11, which is clear and provides most of the refraction power of the eye. Behind the cornea is the anterior chamber 12 that is filled with aqueous humor which is a watery fluid. The eye further includes an iris 13 which forms a pupil 14 that varies in size, typically from less than 2 mm. to about 8 mm. in diameter as the iris 13 expands and contracts to control the amount of light admitted to the eye. This range generally decreases with age. Immediately beyond the pupil is the natural crystalline lens 15 which changes shape to focus the eye. The lens 15 is supported and held in place by ligaments 16. Behind the lens 15 is a chamber 18 which is filled with the vitreous humor. At the back of the eye is the retina 20 where images are focused by a healthy eye and carried by the optic nerve 22 to the brain. The posterior chamber is in the area between the lens 15 and the iris 13.

The cornea 11 and crystalline lens 15 work together to bring images in focus at the retina 20, with the pupil 14 functioning as an aperture to permit the proper amount of light to reach the retina 20.

The cornea 11 is the major optical system of the eye. Although the refractive index of the natural lens 15 is actually higher than that of the cornea 11, its effective index and thereby its power is about one-half of the cornea because the lens is in contact with a higher index liquid, i.e., the vitreous and aqueous humor, than the cornea, which is in contact with the low index of air.

The crystalline lens 15, through its unique ability to accommodate, or change shape, can adjust its effective focal length for viewing near or distant objects. Depending on the age of the individual, the lens 15 can, by accommodation, add up to 14 diopters of refraction power.

The quality of image produced by a healthy lens 15 depends on its ability to accommodate, on its refraction index gradient (the nucleus of the lens has a higher refractive index than the cortex, so peripheral rays passing through only the cortex are refracted less than those passing through both the cortex and nucleus in the middle of the lens), and on the fact that the natural lens is aspherically shaped. The curvature of the lens tends to flatten peripherally, and does so to a greater extent when lens power increases during accommodation.

The healthy lens 15 has intrinsic self-correcting focusing mechanisms, many of which become impaired with age. The older eye has reduced lens accommodation function and impaired iris-pupil reflex. In the cataractous eye, light transmission is drastically reduced or nearly nonexistent.

After the natural lens is removed in cataract surgery, the patient loses the function of a very important optical system. The eye loses the lens' ability to accommodate, its refraction index gradient, and its aspheric focusing function.

With the lens 15 removed, light rays focus beyond the retina 20 with a resultant loss of vision. This can be corrected by spectacles, contact lenses, or intraocular lenses, with intraocular lenses generally being preferred.

The intraocular lens replaces the cataractous crystalline lens, and, like the natural lens, uses the phenomenon of refraction to focus light rays passing through it.

Standard intraocular lens designs utilize spheric power curves. The Gaussian theory of optics, or "thin lens equation", says that light rays, passing through a spheric lens, will be imaged on the central optical axis. This is shown in FIG. 2 where light rays 24 from a point source pass through a spheric lens 25 and converge on the central axis 26 at an image point 27.

The Gaussian theory, however, gives a rather crude picture of the path of a ray of light from object to image. In spheric lenses, rays of light that make various angles with respect to the optical axis may not be focused to the same unique focal point. Analysis of geometrical optics by ray tracing demonstrates that the directions a light ray takes will depart from the predictions of Gaussian theory. These departments are called aberrations and produce an aberrated image.

Spherical aberration is a significant problem for many intraocular lens users. This is the inherent aberration of spheric lenses caused by the fact that the lens has a longer focal length for rays near the center than for rays passing through the outer zone.

FIG. 3 is a diagram showing the focusing of the various rays 30 at different points upon passing through a spheric lens 31. The rays are focused in a zone 32 which defines a circle of confusion 33. Spherical aberration is commonly attributed by surgeons as the cause of patient complaints of visual flare, glare, halo or "dazzle" and "glitter".

There is, then, no one focal length for a spheric lens but rather a focal zone or region. This zone forms the circle of confusion 33 or "blur circle". When the iris aperture is at a normal daylight dilation (approximately 2 to 3 mm.), these aberrations are not as pronounced because the outer zone of the lens is blocked off by the iris. Spherical aberration becomes a more acute problem in low light conditions, for example, at night, when the iris is dilated to allow as much light as possible into the eye.

The lens of this invention is aspheric and eliminates most of the spherical aberration by using progressively longer radii toward the outer zone of the lens.

Referring to FIGS. 4 and 5, there is shown a plan view (FIG. 4) and a side view (FIG. 5) of an exemplary intraocular lens in accordance with this invention.

The lens 40 of the illustrated embodiment is a "planoconvex" lens, i.e., it has a convex surface 41 on one side and a flat or a planar surface 42 on its other side. If desired, lenses having other design configurations can be provided in accordance with practice of this invention.

Lens 40 has a varying radius of curvature from the apex 43 to the outer edge 44, with the radius being longer at the edge. The varying may be continuous from the apex to the edge or may be interrupted with a selected radius being the same over a particular area. For example, since rays through the central zone of approximately 3 mm diameter of the lens cause very little, if any, of the aberration, this portion may be at the apical radius and thus spherical. Preferably, for smoothness of change, however, the change in radius begins adjacent the apex.

To provide correction for the majority of aphakic patients a family of aspheric lens of this invention will have apical radii between 6.2 mm and 15.51 mm with refraction power between 25 and 10 diopters in the eye and preferably available in ¼ diopter steps.

The aspheric lens of this invention for replacing the normal crystalline lens preferably has a curvature that varies from the apex to the edge. One variation found to be effective for aspheric intraocular lenses in accordance with this invention is where the sag value Z, is determined by the following equation:

$$Z = \frac{C_a Y^2}{1 + [1 - (1 + k)(C_a)^2 Y^2]^{\frac{1}{2}}} + AY^4 + BY^6 + CY^8 + DY^{10}$$

where:
  $C_a$ = apical curvature;

k = conic constant to yield either an ellipse or a hyperbola;

A, B, C, and D = coefficients for varying the curvature from the apex to the edge; and Y = distance normal to the optical axis of the lens through the apex as shown in FIG. 6.

For example, an aspheric intraocular lens having 18.0 diopter power in the eye in accordance with this invention has an apical curvature of 0.11628 mm., a conic constant of 0.000119 and coefficients A through D of $-0.276075 \times 10^{-3}$; $-0.324511 \times 10^{-5}$; $0.268191 \times 10^{-7}$; and $-0.145071 \times 10^{-9}$, respectively.

The following is a chart of the conic constants and coefficient found to produce a complete family of effective aspheric lens.

| Diopter (Eye) | Ca × $10^{-2}$ | K × $10^{-3}$ | A × $10^{-3}$ | B × $10^{-5}$ | C × $10^{-9}$ | D × $10^{-10}$ |
|---|---|---|---|---|---|---|
| 10 | 6.447 | .265 | −.192807 | −.10861 | −.203377 | .507039 |
| 10.5 | 6.77 | .299 | −.194550 | −.115792 | −.869791 | .522880 |
| 11 | 7.092 | .314 | −.196336 | −.123124 | −1.58687 | .520648 |
| 11.5 | 7.415 | .318 | −.198817 | −.131235 | −2.36760 | .509791 |
| 12 | 7.737 | .320 | −.201688 | −.139867 | −3.21878 | .489171 |
| 12.5 | 8.059 | .307 | −.205027 | −.149196 | −4.16882 | .462950 |
| 13 | 8.382 | .298 | −.208396 | −.158830 | −5.22122 | .424082 |
| 13.5 | 8.705 | .299 | −.212971 | −.170045 | −6.41432 | .381238 |
| 14 | 9.027 | .307 | −.217322 | −.181376 | −7.72415 | .316264 |
| 14.5 | 9.349 | .304 | −.222617 | −.194216 | −9.19654 | .226656 |
| 15 | 9.671 | .288 | −.228381 | −.208100 | −10.8498 | .113574 |
| 15.5 | 1.000 | .131 | −.234722 | −.223455 | −12.7517 | −.0361902 |
| 16 | 1.0317 | .116 | −.241366 | −.239526 | −14.8455 | −.0194536 |
| 16.5 | 10.627 | .118 | −.249590 | −.258260 | −17.2455 | −.380321 |
| 17 | 10.965 | .120 | −.257318 | −.277884 | −20.0191 | −.676902 |
| 17.5 | 11.287 | .138 | −.265935 | −.299238 | −23.1081 | −.997463 |
| 18 | 11.628 | .119 | −.276075 | −.324511 | −26.8191 | −1.45071 |
| 18.5 | 11.933 | .115 | −.286278 | −.349943 | −30.6623 | −1.92666 |
| 19 | 12.255 | .093 | −.297730 | −.379195 | −35.2485 | −2.54846 |
| 19.5 | 12.579 | −209.862 | −.257701 | −.337117 | −30.9202 | −1.58611 |
| 20 | 12.903 | −209.861 | −.266800 | −.362553 | −34.8611 | −2.19214 |
| 20.5 | 13.288 | −216.035 | −.274240 | −.386696 | −39.2435 | −2.62190 |
| 21 | 13.55 | −23.2098 | −.280288 | −.410766 | −43.3719 | −3.28125 |
| 21.5 | 13.87 | −23.2093 | −.290679 | −.441681 | −48.8705 | −4.06198 |
| 22 | 14.184 | −23.2094 | −.302648 | −.476935 | −55.1714 | −4.98135 |
| 22.5 | 14.514 | −23.2095 | −.315256 | −.515630 | −62.4471 | −6.11013 |
| 23 | 14.837 | −23.2145 | −.332809 | −.566820 | −71.6961 | −7.46951 |
| 23.5 | 15.155 | −24.2738 | −.338602 | −.595568 | −78.2638 | −8.73609 |
| 24 | 15.48 | −24.2737 | −.355016 | −.648247 | −88.88159 −10.5606 | |
| 24.5 | 15.798 | −24.2745 | −.371194 | −.702356 | −100.112 | −12.6698 |
| 25. | 16.129 | −25.7839 | −.381465 | −.749158 | −110.796 | −14.5862 |

The visual acuity of aspheric intraocular lenses is significantly better than spherical intraocular lenses above 3 mm of pupil opening as shown by a modulation transfer function (MTF) analysis using the MIL-SPEC eye model (MIL-HDBK-141; 1962). MTF describes the loss of visual contrast caused by an optical system for various spatial frequencies and pupil diameters.

Such an analysis was performed by using a monochromatic light source of 550 nm (green light) at which the peak sensitivity of the human eye in normal daylight is realized. The following are the comparative results in line pairs per millimeter for a 50% MTF which have been computed for an on-axis image of a target placed 20 feet in front of the eye model.

| Entrance Pupil Diameter Or Iris Opening | Spherical Intraocular Lens | Aspherical Intraocular Lens |
|---|---|---|
| 2 mm | 85 lp/mm | 82 lp/mm |
| 3 mm | 110 | 122 |
| 4 mm | 70 | 164 |
| 5 mm | 32 | 205 |
| 6 mm | 17 | 248 |

Thus, the advantages of aspheric intraocular lenses over spheric intraocular lenses is evident. Further, an aspheric intraocular lens is, in general, thinner in thickness than a spheric intraocular lens, and consequently is lighter.

Although this invention has been described in detail with reference to certain versions thereof, it will be understood that variations and modifications can be effected within the spirit and scope of this invention described above and defined in the following claims.

What is claimed:

1. An intraocular lens for implantation in the human eye comprising a lens having at least one curved surface with a radius of curvature that is longer at the edge than at the apex, wherein the radius of curvature in the area up to 1.5 mm from the apex is constant.

2. An intraocular lens for implantation in the human eye comprising a lens having at least one curved surface with a radius of curvature that varies from the apex to the edge according to the equation for the sag value Z of $$Z = \frac{Ca\, Y^2}{1 + [1 - (1 + k)(Ca)^2 Y^2]^{\frac{1}{2}}} + AY^4 + BY^6 + CY^8 + DY^{10}$$

where Ca is the apical curvature; k is a conic constant; A, B, C, and D are coefficients and Y is the distance normal to the optical axis of the lens through the apex and the parameters are selected to provide substantially the same focal length for all diameters of the lens.

3. An intraocular lens in accordance with claim 2 wherein the apical radius of curvature is between 6.2 and 15.51 mm.

4. An intraocular lens in accordance with claim 2 wherein the refractive power at the apex is between 10 and 25 diopters in the eye.

5. An intraocular lens in accordance with claim 2 wherein the lens is plano convex.

6. An intraocular lens for implantation in the human eye comprising a lens having at least one curved surface wherein the curvature of the surface varies from the apex to the edge according to the equation for the SAG value Z of $$Z = \frac{Ca\, Y^2}{1 + [1 - (1 + k)(Ca)^2 Y^2]^{\frac{1}{2}}} + AY^4 + BY^6 + CY^8 + DY^{10}$$

where: Ca is the apical curvature, k is a conic constant; A, B, C, and D are coefficients and Y is the distance normal to the optical axis of the lens through the apex and wherein the apical curvature, a conic constant and coefficients for each diopter of lens are selected from the following:

| Diopter (Eye) | Ca × $10^{-2}$ | K × $10^{-3}$ | A × $10^{-3}$ | B × $10^{-5}$ | C × $10^{-9}$ | D × $10^{-10}$ |
|---|---|---|---|---|---|---|
| 10 | 6.447 | .265 | −.192807 | −.10861 | −.203377 | .507039 |
| 10.5 | 6.77 | .299 | −.194550 | −.115792 | −.869791 | .522880 |
| 11 | 7.092 | .314 | −.196336 | −.123124 | −1.58687 | .520648 |
| 11.5 | 7.415 | .318 | −.198817 | −.131235 | −2.36760 | .509791 |
| 12 | 7.737 | .320 | −.201688 | −.139867 | −3.21878 | .489171 |
| 12.5 | 8.059 | .307 | −.205027 | −.149196 | −4.16882 | .462950 |
| 13 | 8.382 | .298 | −.208396 | −.158830 | −5.22122 | .424082 |
| 13.5 | 8.705 | .299 | −.212971 | −.170045 | −6.41432 | .381238 |
| 14 | 9.027 | .307 | −.217322 | −.181376 | −7.72415 | .316264 |
| 14.5 | 9.349 | .304 | −.222617 | −.194216 | −9.19654 | .226656 |
| 15 | 9.671 | .288 | −.228381 | −.208100 | −10.8498 | .113574 |
| 15.5 | 1.000 | .131 | −.234722 | −.223455 | −12.7517 | −.0361902 |
| 16 | 1.031 | .116 | −.241366 | −.239526 | −14.8455 | −.0194536 |
| 16.5 | 10.627 | .118 | −.249590 | −.258260 | −17.2455 | −.380321 |
| 17 | 10.965 | .120 | −.257318 | −.277884 | −20.0191 | −.676902 |
| 17.5 | 11.287 | .138 | −.265935 | −.299238 | −23.1081 | −.997463 |
| 18 | 11.628 | .119 | −.276075 | −.324511 | −26.8191 | −1.45071 |
| 18.5 | 11.933 | .115 | −.286278 | −.349943 | −30.6623 | −1.92666 |
| 19 | 12.255 | .093 | −.297730 | −.379195 | −35.2485 | −2.54846 |
| 19.5 | 12.579 | −209.862 | −.257701 | −.337117 | −30.9202 | −1.58611 |
| 20 | 12.903 | −209.861 | −.266800 | −.362553 | −34.8611 | −2.19214 |
| 20.5 | 13.288 | −216.035 | −.274240 | −.386696 | −39.2435 | −2.62190 |
| 21 | 13.55 | −23.2098 | −.280288 | −.410766 | −43.3719 | −3.28125 |
| 21.5 | 13.87 | −23.2093 | −.290679 | −.441681 | −48.8705 | −4.06198 |
| 22 | 14.184 | −23.2094 | −.302648 | −.476935 | −55.1714 | −4.98135 |
| 22.5 | 14.514 | −23.2095 | −.315256 | −.515630 | −62.4471 | −6.11013 |
| 23 | 14.837 | −23.2145 | −.332809 | −.566820 | −71.6961 | −7.46951 |
| 23.5 | 15.155 | −24.2738 | −.338602 | −.595568 | −78.2638 | −8.73609 |
| 24 | 15.48 | −24.2737 | −.355016 | −.648247 | −88.88159 | −10.5606 |
| 24.5 | 15.798 | −24.2745 | −.371194 | −.702356 | −100.112 | −12.6698 |
| 25 | 16.129 | −25.7839 | −.381465 | −.749158 | −110.796 | −14.5862 |

* * * * *